United States Patent [19]

Williams et al.

[11] Patent Number: 5,198,219
[45] Date of Patent: Mar. 30, 1993

[54] ATTRACTIONS FOR THE ROSE CHAFTER MACRODACTYLUS SUBSPINOSUS (F.)

[75] Inventors: Roger N. Williams, Wooster; Dan S. Fickle, Burbank, both of Ohio; Terrence P. McGovern, deceased, late of Bowie, Md., by Mary Jo McGovern, sole heir

[73] Assignee: The United States of America as represented by the Secretary of Agriculture, Washington, D.C.

[21] Appl. No.: 626,934

[22] Filed: Dec. 13, 1990

[51] Int. Cl.$^5$ ............................................. A01N 25/00
[52] U.S. Cl. ..................................... 424/405; 424/84; 424/409
[58] Field of Search ........................... 424/405, 84, 409

[56] References Cited

U.S. PATENT DOCUMENTS

| | | | |
|---|---|---|---|
| 3,931,413 | 1/1976 | Frick et al. | 514/558 |
| 4,152,422 | 5/1979 | Ohinata et al. | 424/84 |
| 4,877,607 | 10/1989 | McGovern et al. | 424/84 |

OTHER PUBLICATIONS

Guerin et al., Electroantennogram Responses of Carrot Fly to volatile plant components, Physiological Entom. 5(2):111–120 (1980).
Williams et al., Lab and Field Eval. of insecticides to Protect Grape Clusters From Adult Rose Chafer, J. Econ. Entom. 72(4):583–586 (1979).
R. N. Williams and K. V. Miller, Field Assay to Determine Attractiveness of Various Aromatic Compounds to Rose Chafer Adults, J. Econ. Entomol. 75:196–198 (1982).
R. N. Williams, T. P. McGovern, and M Klein, Evaluation of Aromatic Compounds and Virgin Females as Attractants for Rose Chafer, Research Circular 272, Fruit Crops, pp. 33–40 (1982).
R. N. Williams, T. P. McGovern, M. G. Klein, and D. S. Fickle, Rose Chafer (Coleoptera: Scarabaeidae): Improved Attractants for Adults, J. Econ. Entomol. 83: 111–116 (199).
R. A. Wilson et al., Use of 1-Nonen-3-ol for Repelling Houseflies, U.S. Pat No. 4,693,890, Sep. 15, 1987; Chemical Abstracts 107: Abstr. 193075n (1987).
R. Rossi et al., (Z)-6-Nonen-1-ol and Related Compounds as Attractants of the Olive Fruit Fly, *Dacus oleae* (Gmelin) [Diptera: Trypetidae], Gazz. Chim. Ital. 108: 709–712 (1978); Chemical Abstracts 91: Abstr. 91099g (1979).
K. Ohinata, Attractant for Male Mediterranean Fruit Fly, U.S. Pat. Appl. Ser. No. 875,049, 10 pages (Jul. 7, 1978); Chemical Abstracts 90: Abstr. 98575x (1979).

*Primary Examiner*—Thurman K. Page
*Assistant Examiner*—Robert H. Harrison
*Attorney, Agent, or Firm*—M. Howard Silverstein; Randall E. Deck; John D. Fado

[57] ABSTRACT

Compositions of trans-2-nonenol were found to effectively attract rose chafter, *Macrodactylus subspinosus* (F.). The trans-2-nonenol may be used alone or in combination with one or more organic compounds including: (1) an organic acid component selected from the group of valeric acid, hexanoic acid, and mixtures thereof, (2) an ester component comprising octyl butyrate, and/or (3) an α-ionone component. By attracting the beetles to field traps, the attractants are useful for the monitoring and control of these agricultural pests.

12 Claims, No Drawings

ATTRACTIONS FOR THE ROSE CHAFER *MACRODACTYLUS SUBSPINOSUS* (F.)

BACKGROUND OF THE INVENTION

1. Field of the Invention

The rose chafer, *Macrodactylus subspinosus* (F.) is a serious pest of fruit crops, ornamentals, and flowers in eastern North America. Grapevines are a favorite food of the beetles. They begin their attack at blossom time and devour blossoms and newly set fruit, often destroying an entire crop. Other known host plants are peony, rose, blackberry, raspberry, pear, apple, plum, cherry, corn, Scots pine, and many ornamentals. At present, there is no attractant used for monitoring and possibly controlling adult chafers. This invention relates to compositions that are strongly attractive to rose chafers.

2. Description of the Prior Art

Trapping of the rose chafer was first reported by Johnson [Conn. Agr. Exp. Sta. Bull. 434: 314 (1940)]; however, the attractant used was not named. Williams et al. [J. Econ. Entomol. 75: 196-198 (1982)] disclose that valeric acid and hexanoic acid (caproic acid) are individually attractive to the rose chafer. They also teach that a binary mixture of eugenol and hexanoic acid is attractive to the chafer, but that the attraction of the mixture is due to hexanoic acid alone and that there is no advantage to using the mixture. Williams et al. [Research Circular 272, Fruit Crops, pp. 38-40 (1982)] also tested a large number of acids, anhydrides, acid chlorides, and aldehydes individually as chafer attractants, but none were found superior to valeric acid and hexanoic acid.

SUMMARY OF THE INVENTION

We have now surprisingly found that compositions including trans-2-nonenol are potent attractants for the rose chafer, *Macrodactylus subspinosus* (F.). The trans-2-nonenol may be used alone, or in combination with one or more certain organic compounds including: (1) an organic acid component selected from the group of valeric acid, hexanoic acid, and mixtures thereof, or (2) an ester component comprising octyl butyrate, or (3) α-ionone, or (4) mixtures thereof.

In accordance with this discovery, it is an object of the invention to provide new compositions for attracting rose chafers as an aid to insect control measures.

Another object of the invention is to provide a means for increasing the effectiveness of insect traps for monitoring or suppressing rose chafer populations.

Other objects and advantages of this invention will become obvious from the ensuing description.

DETAILED DESCRIPTION OF THE INVENTION

According to this invention, there is provided a composition for attracting the rose chafer, *Macrodactylus subspinosus*, which includes trans-2-nonenol (trans-2-nonen-1-ol). While the trans-2-nonenol may be used alone, in the preferred embodiment insect attraction is substantially increased when the trans-2-nonenol is used in combination with one or more organic compounds including: (1) an organic acid component selected from the group of valeric acid, hexanoic acid, and mixtures thereof, (2) an ester component comprising octyl butyrate, (3) α-ionone, or (4) mixtures of these acid, ester and/or ionone components. Other alcohols, such as 1-octanol, and 1-nonanol, or secondary alcohols and unsaturated alcohols, can also be used.

Without desiring to be limited thereto, the trans-2-nonenol compositions encompassed herein are effective in controlling the rose chafer, *Macrodactylus subspinosus* (F.).

Suitable formulations of the trans-2-nonenol include trans-2-nonenol in crude or impure form, or in substantially pure form. However, as a practical matter, it is expected that substantially pure trans-2-nonenol will be formulated with an inert carrier, and optionally with the above-noted acid, ester, and/or ionone components, for use as an insect attractant composition. The practitioner skilled in the art will recognize that the trans-2-nonenol and these acid, ester and/or ionone components may be formulated in a single or separate compositions. Alternatively, the trans-2-nonenol composition may be further formulated with other insect attractants such as pheromones, insect extracts containing pheromones, or host plant volatiles.

The amount of trans-2-nonenol is selected to provide an effective attraction of the insects. The effective amount is defined as that quantity of attractant that attracts the insects to the location of a bait at a rate significantly higher than the attraction to a nonbaited location. Effective concentrations of the trans-2-nonenol in the composition may vary between about 0.1 and 99.9%. Suitable amounts and concentrations may be readily determined by the practitioner skilled in the art, and will of course vary with the size of the area to be treated; environmental conditions such as temperature, humidity, and wind conditions; the type of vehicle or carrier; and the insect population. When employed in combination with the above-noted acid, ester and/or ionone components, the ratio and absolute amounts of all active ingredients may also vary and are similarly selected to provide an effective attraction of the insects to the composition.

The trans-2-nonenol of this invention is readily available from commercial sources. The aliphatic acids, esters, and α-ionone contemplated by the invention are also available from commercial sources.

The attractants may be used in a number of ways, such as in combination with an effective amount of a pesticide to kill the target insects, and in traps to monitor population changes. Precise monitoring will enable growers to reduce the number of insecticide applications when populations are low. Other formulations and methods of use will be obvious to those in the art. In practice, an attractant is used as a trap bait or is otherwise applied to the locus of or in the vicinity of infestation in an amount effective to attract the beetle. As above, an effective amount is defined as that quantity of attractant that attracts the insects to the location of a bait at a rate significantly higher than the attraction to a nonbaited location. Factors such as population density, precipitation, temperature, wind velocity, and release rate will influence the actual number of beetles trapped.

It is envisioned that the attractants would be effective in monitoring or controlling beetle populations when used in conjunction with any type of appropriate trap or attractant disseminator as known in the art. The attractant can be disseminated by any suitable means such as by impregnation of wicking material or by use of a deodorant dispenser. Further, the components of the attractant may be combined in a single dispenser provided within a single trap, or provided separately in a plurality of dispensers, all within a single trap. The attractant can be applied to the device undiluted, or volatilization can be controlled or retarded by inclusion of an oleaginous extender such as trioctanoin. Trioctanoin alone is unattractive to the rose chafer. Controlled, slow release may also be effected by encapsulation or absorption into a porous substrate.

The following examples are intended only to further illustrate the invention and are not intended to limit the scope of the invention, which is defined by the claims.

EXAMPLE 1

The attraction of rose chafers toward valeric acid compositions including trans-2-nonenol as compared with various other alcohols was established under field conditions. The field test was conducted in a sandy field adjacent to a Concord vineyard located near North Kingsville, Ohio, in an area known for very high populations of rose chafers. The test materials, including valeric acid with trans-2-nonenol, listed in Table I were exposed by saturating deodorant dispensers, Loral Poly-Cons (Trece, Inc., Salinas, Calif.), with about 5 ml of the candidate lure. A single opened dispenser was placed inside the perforated attractant dispenser of a metal Japanese beetle trap fitted with a collector for holding beetles. Each lure was replicated four times in a randomized complete-block design in which the traps were suspended from steel rods 1 m above ground and spaced in rows 8 m apart. Traps within a row were 10 m apart. Beetle catches were recorded at the end of each trapping period of 3 or 4 days, and traps were rebaited after each trapping period. An untreated control was included in all tests. Data were subjected to analysis of variance, and means were compared by Duncan's [Biometrics 11: 1–42 (1955)] multiple range test ($P \leq 0.05$).

EXAMPLE 2

Selected Mixtures

The procedure of Example 1 was repeated at Castalia, Ohio, with the test materials listed in Table II. The data indicate that compositions including trans-2-nonenol, especially in combination with one or more of octyl butyrate, hexanoic acid, and/or valeric acid, are significantly more attractive than compositions lacking trans-2-nonenol.

EXAMPLES 3–5

The procedure of Example 1 was subsequently repeated on three separate occasions at North Kingsville, Ohio, with the lure formulations listed in Tables III–V, except that the α-ionone component of treatment numbers 26 and 27 in Table III was provided in a separate dispenser from the other components, for a total of two dispensers within a single trap. The formulations including trans-2-nonenol were effective as attractants for the rose chafer. Formulations also including α-ionone, hexanoic acid, valeric acid and/or octyl-butyrate together with trans-2-nonenol (and especially those containing all five components) were particularly effective as attractants for the rose chafer.

It is understood that the foregoing detailed description is given merely by way of illustration and that modifications and variations may be made therein without departing from the spirit and scope of the invention.

TABLE I

| Treatment No. | Candidate Lure | Mean No. of Beetles Trapped[a] |
|---|---|---|
| 1 | Valeric acid + trans-2-nonenol 1:1 | 142.00 a |
| 2 | Valeric acid + cis-2-nonenol 1:1 | 64.75 b |
| 3 | Valeric acid + trans-2-octenol 1:1 | 57.25 b |
| 4 | Valeric acid + cis-6-nonenol 1:1 | 43.00 b |
| 5 | Valeric acid + 1-nonanol 1:1 (Std.) | 40.50 b |
| 6 | Valeric acid + cis-3-nonenol 1:1 | 34.25 b |
| 7 | Valeric acid + cis-3-octenol 1:1 | 21.50 b |
| 8 | Valeric acid + 3-octen-2-ol 1:1 | 11.75 b |
| 9 | Iso-safrole | 10.25 b |
| 10 | Safrole | 4.25 b |

Means within a column followed by the same letters are not statistically different.
[a] $F = 4.00$; $df = 9, 27$; $P \leq 0.05$.

TABLE II

| Treatment No. | Candidate Lure | Ratio | Beetles Collected Mean |
|---|---|---|---|
| 1 | Valeric acid + hexanoic acid + octyl butyrate + 1-nonanol (Std.) | 1:1:1:1 | 890.50 bcde |
| 2 | Valeric acid + hexanoic acid + octyl butyrate + trans-2-nonenol | 1:1:1:1 | 1155.25 abc |
| 3 | Valeric acid + octyl butyrate + 1-nonanol + 1-octanol | 1:1:1:1 | 809.25 bcde |
| 4 | Valeric acid + octyl butyrate + trans-2-nonenol + 1-octanol | 1:1:1:1 | 821.50 bcde |
| 5 | Hexanoic acid + octyl butyrate + 1-nonanol + 1-octanol | 1:1:1:1 | 511.50 cde |
| 6 | Hexanoic acid + octyl butyrate + trans-2-nonenol + 1-octanol | 1:1:1:1 | 1081.25 abcd |
| 7 | Valeric acid + octyl butyrate + 1-nonanol | 1:1:1 | 825.25 bcde |
| 8 | Valeric acid + octyl butyrate + 1-octanol | 1:1:1 | 435.75 cde |
| 9 | Valeric acid + octyl butyrate + trans-2-nonenol | 1:1:1 | 1139.00 abcd |
| 10 | Hexanoic acid + octyl butyrate + 1-octanol | 1:1:1 | 449.75 cde |
| 11 | Hexanoic acid + octyl butyrate + 1-nonanol | 1:1:1 | 857.00 bcde |
| 12 | Hexanoic acid + octyl butyrate + trans-2-nonenol | 1:1:1 | 1446.00 ab |
| 13 | Valeric acid + 1-nonanol (Std.) | 1:1 | 773.50 bcde |
| 14 | Valeric acid + trans-2-nonenol | 1:1 | 1669.00 a |
| 15 | Octyl butyrate + 1-nonanol | 1:1 | 423.50 cde |
| 16 | Octyl butyrate + trans-2-nonenol | 1:1 | 527.75 cde |
| 17 | Valeric acid + hexanoic acid | 1:1 | 262.50 e |
| 18 | 1-Nonanol | single | 209.00 e |
| 19 | trans-2-Nonenol | single | 880.00 bcde |
| 20 | Valeric acid | single | 359.75 de |
| 21 | Hexanoic acid | single | 522.25 cde |
| 22 | Control (untreated) | — | 135.00 e |

Means followed by the same letter in the same column are not statistically different as determined by Duncan's multiple range test ($P \leq 0.05$).

TABLE III

| Treatment No. | Candidate Lure | Ratio | Beetles Collected (Entire Season) Mean | |
|---|---|---|---|---|
| 1 | Control (untreated) | — | 89.00 | hi |
| 2 | Hexanoic acid | single | 102.50 | hi |
| 3 | Valeric acid | single | 154.75 | fghi |
| 4 | Hexanoic acid + valeric acid | 1:1 | 109.50 | ghi |
| 5 | Hexanoic acid + 1-nonanol | 1:1 | 130.50 | ghi |
| 6 | Octyl butyrate | single | 185.50 | fghi |
| 7 | Alpha-ionol | single | 163.50 | fghi |
| 8 | Alpha-ionol + hexanoic acid | 1:1 | 241.75 | fghi |
| 9 | Alpha-ionol + valeric acid | 1:1 | 203.25 | fghi |
| 10 | Beta-ionone | single | 74.50 | hi |
| 11 | Beta-ionol | single | 35.75 | i |
| 12 | Beta-ionone + beta-ionol | 1:1 | 50.50 | i |
| 13 | Alpha-ionone | single | 634.25 | bcde |
| 14 | Alpha-ionone + hexanoic acid | 1:1 | 892.75 | b |
| 15 | Alpha-ionone + valeric acid | 1:1 | 459.50 | cdefg |
| 16 | Alpha-ionone + trans-2-nonenol | 1:1 | 414.75 | cdefgh |
| 17 | Alpha-ionone + cis-2-nonenol | 1:1 | 347.75 | defghi |
| 18 | Alpha-ionone + alpha-ionol | 1:1 | 331.25 | defghi |
| 19 | Alpha-ionone + hexanoic acid + valeric acid | 1:1:1 | 698.25 | bc |
| 20 | Alpha-ionone + hexanoic acid + valeric acid + octyl butyrate + trans-2-nonenol | 1:1:1:1:1 | 1305.00 | a |
| 21 | trans-2-nonenol | single | 111.75 | ghi |
| 22 | trans-2-nonenol + hexanoic acid | 1:1 | 314.00 | efghi |
| 23 | trans-2-nonenol + valeric acid | 1:1 | 415.75 | cdefgh |
| 24 | trans-2-nonenol + hexanoic acid + valeric acid | 1:1:1 | 632.75 | bcde |
| 25 | trans-2-nonenol + hexanoic acid + valeric acid + octyl butyrate | 1:1:1:1 | 493.50 | cdef |
| 26 | (Alpha-ionone) + (trans-2-nonenol) | 1:1 | 596.50 | bcde |
| 27 | (Alpha-ionone) + (hexanoic acid + valeric acid + octyl butyrate + trans-2-nonenol) | 1:1:1:1:1 | 664.25 | bcd |
| 28 | Hexanoic acid + valeric acid + octyl butyrate + 1-nonanol | 1:1:1:1 | 321.75 | defghi |

Means followed by the same letter in the same column are not statistically different as determined by Duncan's multiple range test ($P \leq 0.05$).

TABLE IV

| Treatment No. | Candidate Lure | Ratio | Mean No. of Beetles/ Trapping Period (Entire Season) |
|---|---|---|---|
| 12 | Alpha-ionone + hexanoic acid | 1:1 | 249.63 a |
| 20 | Alpha-ionone + hexanoic acid + valeric acid + trans-2-nonenol | 1:1:1:1 | 239.75 ab |
| 9 | Alpha-ionone + 1% 765 Tinuvin | 1:1 | 197.13 abc |
| 18 | Alpha-ionone + hexanoic acid + valeric acid | 1:1:1 | 194.75 abc |
| 21 | Alpha-ionone + hexanoic acid + valeric acid + octyl butyrate + 1-nonanol | 1:1:1:1:1 | 194.63 abc |
| 19 | Alpha-ionone + hexanoic acid + valeric acid + octyl butyrate | 1:1:1:1 | 192.38 abc |
| 15 | Alpha-ionone + trans-2-nonenol | 1:1 | 179.88 abc |
| 16 | Alpha-ionone + octyl butyrate | 1:1 | 173.75 abc |
| 13 | Alpha-ionone + valeric acid | 1:1 | 172.13 abc |
| 10 | Alpha-ionone (75%) + trioctanoin (25%) | 3:1 | 162.00 abcd |
| 17 | Alpha-ionone + octyl butyrate + trans-2-nonenol | 1:1:1 | 151.50 abcde |
| 14 | Alpha-ionone + 1-nonanol | 1:1 | 151.25 abcde |
| 22 | Hexanoic acid + valeric acid + octyl butyrate + trans-2-nonenol | 1:1:1:1 | 136.63 bcdef |
| 8 | Alpha-ionone | single | 116.75 cdef |
| 11 | Alpha-ionone (50%) + trioctanoin (50%) | 1:1 | 106.75 cdef |
| 23 | Hexanoic acid + valeric acid + octyl butyrate + 1-nonanol | 1:1:1:1 | 87.25 cdef |
| 2 | Hexanoic acid | single | 56.75 def |
| 7 | trans-2-nonenol | single | 47.50 ef |
| 3 | Valeric acid | single | 41.75 f |
| 5 | Octyl butyrate | single | 40.13 f |
| 1 | Control (untreated) | — | 36.50 f |
| 4 | Hexanoic acid + valeric acid | 1:1 | 34.00 f |
| 6 | 1-Nonanol | single | 26.75 f |

Means followed by the same letter in the same column are not statistically different as determined by Duncan's multiple range test ($P \leq 0.05$).

TABLE V

| Treatment No. | Candidate Lure | Ratio | Mean No. of Beetles/ Trapping Period (Entire Season) |
|---|---|---|---|
| 18 | Valeric acid + hexanoic acid + octyl butyrate + trans-2-nonenol + alpha-ionone | 1:1:1:1:1 | 238.75 a |
| 22 | Valeric acid + hexanoic acid + octyl butyrate + trans-2-nonenol + alpha-ionone | 1:1:1:9:1 | 209.75 ab |
| 23 | Valeric acid + hexanoic acid + octyl butyrate + trans-2-nonenol + alpha-ionone | 1:1:1:1:9 | 197.88 abc |
| 19 | Valeric acid + hexanoic acid + octyl butyrate + trans-2-nonenol + alpha-ionone | 9:1:1:1:1 | 180.25 abcd |
| 20 | Valeric acid + hexanoic acid + octyl butyrate + trans-2-nonenol + alpha-ionone | 1:9:1:1:1 | 167.88 abcd |
| 16 | Valeric acid + hexanoic acid + octyl butyrate + 1-nonanol + alpha-ionone | 1:1:1:9:1 | 162.00 abcd |
| 2 | Valeric acid + hexanoic acid + octyl butyrate + 1-nonanol | 1:1:1:1 | 152.13 abcd |
| 17 | Valeric acid + hexanoic acid + octyl butyrate + 1-nonanol + alpha-ionone | 1:1:1:1:9 | 150.88 abcd |
| 10 | Valeric acid + hexanoic acid + octyl butyrate + trans-2-nonenol | 1:1:9:1 | 148.63 abcd |
| 12 | Valeric acid + hexanoic acid + octyl butyrate + 1-nonanol + alpha-ionone | 1:1:1:1:1 | 141.25 bcde |

TABLE V-continued

| Treatment No. | Candidate Lure | Ratio | Mean No. of Beetles/ Trapping Period (Entire Season) | |
|---|---|---|---|---|
| 8 | Valeric acid + hexanoic acid + octyl butyrate + trans-2-nonenol | 9:1:1:1 | 139.88 | bcde |
| 9 | Valeric acid + hexanoic acid + octyl butyrate + trans-2-nonenol | 1:9:1:1 | 130.38 | bcde |
| 14 | Valeric acid + hexanoic acid + octyl butyrate + 1-nonanol + alpha-ionone | 1:9:1:1:1 | 123.88 | bcde |
| 15 | Valeric acid + hexanoic acid + octyl butyrate + 1-nonanol + alpha-ionone | 1:1:9:1:1 | 118.75 | bcde |
| 13 | Valeric acid + hexanoic acid + octyl butyrate + 1-nonanol + alpha-ionone | 9:1:1:1:1 | 100.88 | cde |
| 7 | Valeric acid + hexanoic acid + octyl butyrate + trans-2-nonenol | 1:1:1:1 | 97.25 | de |
| 5 | Valeric acid + hexanoic acid + octyl butyrate + 1-nonanol | 1:1:9:1 | 95.50 | de |
| 4 | Valeric acid + hexanoic acid + octyl butyrate + 1-nonanol | 1:9:1:1 | 83.50 | de |
| 11 | Valeric acid + hexanoic acid + octyl butyrate + trans-2-nonenol | 1:1:1:9 | 82.63 | de |
| 21 | Valeric acid + hexanoic acid + octyl butyrate + trans-2-nonenol + alpha-ionone | 1:1:9:1:1 | 81.75 | de |
| 6 | Valeric acid + hexanoic acid + octyl butyrate + 1-nonanol | 1:1:1:9 | 81.00 | de |
| 1 | Valeric acid + hexanoic acid + octyl butyrate | 1:1:1 | 49.75 | e |
| 3 | Valeric acid + hexanoic acid + octyl butyrate + 1-nonanol | 9:1:1:1 | 47.13 | e |
| 24 | Check (untreated) | — | 47.00 | e |

Means followed by the same letter in the same column are not statistically different as determined by Duncan's multiple range test ($P \leq 0.05$).

We claim:

1. A composition for attracting insects comprising a mixture of (1) trans-2-nonenol, and (2) an organic acid component selected from the group consisting of valeric acid, hexanoic acid mixtures thereof and wherein the concentration of trans-2-nonenol is between about 0.1 and 99.9%.

2. A composition as described in claim 1 further comprising octyl butyrate.

3. A composition as described in claim 1 further comprising an inert carrier.

4. A composition as described in claim 1, further comprising a pesticide.

5. A method for attracting insects, comprising the step of providing trans-2-nonenol in combination with an organic acid component selected from the group consisting of valeric acid, hexanoic acid, and mixtures thereof, to the locus of said insects, and wherein the concentration of trans-2-nonenol is between about 0.1 and 99.9%.

6. A method as described in claim 5 wherein said insects are rose chafer beetles, *Macrodactylus subspinosus* (F.).

7. A method as described in claim 5 wherein said trans-2-nonenol is further provided in combination with octyl butyrate.

8. A method as described in claim 5 wherein said trans-2-nonenol is further provided in combination with an inert carrier.

9. A method as described in claim 5 wherein said trans-2-nonenol is provided in combination with a pesticide.

10. A method as described in claim 5, wherein said trans-2-nonenol and said organic acid component are combined in a single composition.

11. A method as described in claim 5, wherein said trans-2-nonenol and said organic acid component are in separate compositions.

12. A method for attracting rose chafer beetles, *Macrodactylus subspinosus* (F.), comprising the step of providing trans-2-nonenol to the locus of said rose chafer beetles, *Macrodactylus subspinosus* (F.), in an amount effective to attract said beetles. u

* * * * *